US00PP17822P3

(12) United States Plant Patent
Sproul

(10) Patent No.: US PP17,822 P3
(45) Date of Patent: Jun. 19, 2007

(54) GRANDIFLORA ROSE PLANT NAMED 'WEKSPROULSES'

(50) Latin Name: *Rosa hybrida*
Varietal Denomination: WEKsproulses

(75) Inventor: James A. Sproul, Bakersfield, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 11/285,955

(22) Filed: Nov. 23, 2005

(65) Prior Publication Data

US 2007/0118941 P1 May 24, 2007

(51) Int. Cl.
*A01H 5/00* (2006.01)

(52) U.S. Cl. ..... Plt./130

(58) Field of Classification Search ..... Plt./130, Plt./132
See application file for complete search history.

*Primary Examiner*—Kent Bell
*Assistant Examiner*—Annette H Para
(74) *Attorney, Agent, or Firm*—Christie, Parker & Hale, LLP

(57) ABSTRACT

A new variety of Grandiflora rose suitable for garden decoration, having flowers of warm golden brown coloration.

1 Drawing Sheet

Classification: The present invention relates to a new *Rosa hybrida* plant.

Variety denomination: The new plant has the varietal denomination 'WEKsproulses'.

BACKGROUND OF THE INVENTION

This invention relates to a new and distinct variety of Grandiflora Rose. It has as its seed parent the variety known as 'WEKblusi' (U.S. Plant Pat. No. 10,188) and as its pollen parent the variety known as 'MACivy' (U.S. Plant Pat. No. 8,362).

SUMMARY OF THE INVENTION

Among the features which distinguish the new variety from other presently available and commercial rose cultivars known to the inventor are the following combination of characteristics: its unique warm golden brown flower color, its heavy blush of red coloration on the newly opened petals and its red suffusion on the stipule and the rachis of the young leaf. The plant has an upright and rounded moderately spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKsproulses' may be asexually propagated by budding and grafting. The budding and grafting successfully occurred on the plant/rootstock *Rosa hybrida* cv. 'Dr. Huey'.

COMPARISON WITH PARENTS

The new rose may be distinguished from its seed parent, 'WEKblusi' by the following combination of characteristics: whereas 'WEKsproulses' bears flowers of warm golden brown coloration, 'WEKblusi' bears flowers of silvery lavender coloration. The new variety is classified as a grandiflora rose with an upright and rounded moderately spreading medium height mature growing habit (about 100 to about 130 cm in height), whereas the seed parent is classified as a hybrid tea rose with a significantly taller very upright mature growing habit (about 170 to about 200 cm in height). 'WEKsproulses' bears flowers that have a moderate fruity to somewhat tea fragrance, whereas 'WEKblusi' bears flowers with a significantly stronger penetrating fragrance of damask rose and citrus blossom.

The new variety may be distinguished from its pollen parent, 'MACivy' by the following combination of characteristics: whereas 'WEKsproulses' bears medium sized flowers (about 9.4 to about 14.3 cm in diameter) of warm golden brown coloration, 'MACivy' bears significantly smaller flowers (about 7.0 to about 8.0 cm in diameter) of multi-colored apricot and red coloration. The new variety usually bears its flowers singly, whereas the pollen parent bears its flowers in sprays of generally three to fifteen blooms.

COMPARISON WITH THE CLOSEST COMMERCIALLY AVAILABLE CULTIVAR

The closest commercially available cultivar to the new variety is the pollen parent 'MACivy'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of November. Phenotypic expression may vary with environmental, cultural and climatic conditions, as well as differences in conditions of light and soil.

FLOWER

The new variety usually bears its flowers singly. Flowers are borne on strong medium length stems (about 23 to about 50 cm). Outdoors, the plant blooms abundantly and nearly continuously during the growing season. The flowers have a moderate fruity to somewhat tea fragrance.

BUD

The peduncle is about 3.3 to about 5.6 cm in length, of somewhat heavy caliper (about 0.3 to about 0.5 cm in diameter), and usually erect. It is moderately smooth, with some stipitate glands and few hairs. Peduncle color is between 144A and 141C sometimes lightly suffused, especially on the side exposed to the sun, with between 187B and 183A.

Before the calyx breaks, the bud is about 1.3 to about 1.8 cm in diameter at the widest point, about 1.6 to about 2.4 cm in length, and pointed to somewhat ovoid in shape. The surface of the bud bears few very long foliaceous appendages, usually with slender entire foliaceous parts extending beyond the tip of the bud about ½ or more of its length. Bud color is between 137A and 141B sometimes lightly suffused, especially on the side exposed to the sun, with between 183C and 183B.

The sepals are about 2.6 to about 4.9 cm in length and about 0.8 to about 1.2 cm in width at the widest point. The outer surface color of the sepal is between 137A and 141B sometimes lightly suffused, especially on the side exposed to the sun, with between 183C and 183B. The inner surface color of the sepal is between 137A and 138B and covered with fine wooly tomentum; sepal margins are lined with many stipitate glands and hairs.

The receptacle of the flower is of somewhat short length (about 0.4 to about 0.6 cm) and average in caliper (about 0.8 to about 1.1 cm in diameter). The receptacle is vase shape in form. Its surface is very smooth with thick fleshy walls. The receptacle color is between 144A and 141C.

As the petals open (after the calyx breaks), the bud is about 2.1 to about 2.7 cm in diameter at the widest point, about 2.8 to about 3.2 cm in length, and ovoid in form. On the under surface of the newly opened petals, the color at the base is between 1B and 2B, gradually suffusing toward the edge of the petals with between 199A and 164B usually heavily blushed with between 60A and 53A. On the upper surface of the newly opened petals, the color at the base is between 2A and 3A, gradually suffusing toward the edge of the petals with between 199A and 164B usually heavily blushed with between 60A and 53A.

BLOOM

When fully opened, the bloom ranges from about 9.4 to about 14.3 cm in diameter. Petalage is double with about 23 to 32 petals and about 1 to 7 petaloids irregularly arranged. When partially open, the bloom form is high centered to somewhat cupped, and the petals are moderately tightly spiraled to cupped with petal edges somewhat reflexed outward. When fully open, the bloom form is more cupped, and the petals are loosely cupped with petal edges moderately reflexed outward.

PETALS

The substance of the petals is moderately heavy and of medium thickness, with upper surfaces moderately satiny and under surfaces somewhat shiny. The petals are about 4.0 to about 6.0 cm in length and about 2.9 to about 5.6 cm in width at the widest point. Petal margins are entire.

The outer petals are moderately obovate in shape with rounded apices.

The inner petals are obovate to somewhat oblanceolate in shape with rounded apices.

Petaloids are about 2.3 to about 4.5 cm in length and about 0.9 to about 3.6 cm in width at the widest point. Petaloids are irregularly shaped somewhat oblanceolate to oblong with rounded apices.

NEWLY OPENED FLOWER

On the under surface of the outer petals, the color at the base of the petals is between 9B and 8A, gradually suffusing toward the edge of the petals with between 161D and 159B usually heavily blushed with between 60B and 53B. On the upper surface of the outer petals, the color at the base of the petals is between 9A and 12A, gradually suffusing toward the edge of the petals with between 161C and 159B usually heavily blushed with between 60B and 53A.

On the under surface of the intermediate and inner petals, the color at the base of the petals is between 9B and 8A, gradually suffusing toward the edge of the petals with between 161A and 161C. On the upper surface of the intermediate and inner petals, the color at the base of the petals is between 9A and 12A, gradually suffusing toward the edge of the petals with between 161A and 161D sometimes moderately blushed with between 60B and 53A.

The under and upper surface color of the petaloids are similar in coloration to the upper and under surfaces of the intermediate and inner petals.

The general tonality of the newly opened flower is between 161A and 161D sometimes moderately blushed with between 60B and 53A.

THREE-DAY-OLD FLOWER

On the under surface of the outer petals, the color at the base of the petals is between 9C and 8A, gradually suffusing toward the edge of the petals with between 159C and 159B often moderately blushed with between 60C and 53C. On the upper surface of the outer petals, the color at the base of the petals is between 9C and 12A, gradually suffusing toward the edge of the petals with between 161D and 159C often moderately blushed with between 60C and 53C.

On the under surface of the intermediate and inner petals, the color at the base of the petals is between 9C and 8A, gradually suffusing toward the edge of the petals with between 159C and 159B. On the upper surface of the intermediate and inner petals, the color at the base of the petals is between 9C and 12A, gradually suffusing toward the edge of the petals with between 161D and 159C.

The under and upper surface color of the petaloids are similar in coloration to the upper and under surfaces of the intermediate and inner petals.

The general tonality of the three-day-old flower is between 161D and 159C.

On the spent bloom, the petals usually drop off cleanly.

In November in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 140) and are arranged regularly about the pistils; a few are mixed with petaloids. The filaments are of moderately long length (about 0.9 to about 1.5 cm) most with anthers. Filaments are between 12B and 9B in color sometimes lightly suffused with between 34B and 33B. The anthers are of medium size for the class and all open approximately at the same time. Anther color is between 16A and 16D when immature and between 200A and 163B at maturity. Pollen is abundant and between 16C and 14C in color.

FEMALE REPRODUCTIVE ORGANS

Pistils vary in number (average about 130). The style are moderately even, somewhat long in length (about 0.7 to about 1.0 cm), very thin in caliper and loosely bunched to somewhat separated. Stigma color is between 12C and 14C. Style color is between 4D and 2D sometimes lightly suffused with between 53B and 53C. Ovaries are usually all enclosed in the calyx.

Hips are of moderately short to average length (about 1.2 to about 1.6 cm), globular in form, and between 21B and 23B in color when ripe. The hip surface is very smooth with thick fleshy walls. The sepals are moderately fugacious and usually straight in shape.

The seeds are irregularly rounded, smooth in texture, approximately 3 to about 8 per hip, about 0.4 to about 0.6 cm in diameter at the widest point and between 162B and 163D in color.

FOLIAGE

The compound leaves are usually comprised of three to seven leaflets and are borne abundantly. The five-leaflet leaves are about 7.6 to about 14.1 cm in length and about 6.0 to about 10.7 cm in width at the widest point, moderately heavy to crisp in texture, and moderately glossy in finish. The terminal leaflets are about 3.4 to about 7.5 cm in length and about 2.0 to about 4.4 cm in width at the widest point, shaped oval with acute to somewhat acuminate apices and moderately rounded to acute bases. Their margins are usually simply serrate.

The upper surface color of the mature leaf is between 147A and 135B. The under surface color of the mature leaf is between 146A and 141B. The upper surface color of the young leaf is between 146A and 141B, usually moderately suffused especially on the very edge of the leaf with between 187B and 183A. The under surface color of the young leaf is between 146B and 143C, usually heavily suffused with between 187B and 183A.

The rachis is average in caliper and usually smooth but sometimes moderately rough. The upper side is deeply grooved with few hairs and stipitate glands on the edges of the grooves. The under side of the rachis is usually smooth but sometimes moderately rough with sometimes very few stipitate glands and very few small prickles. The rachis color is between 145A and 147A usually heavily suffused on the young leaf with between 187B and 183A.

The stipules are about 1.0 to about 1.8 cm in length and very wide (about 0.4 to about 1.1 cm) with moderately long straight points that usually turn out at an angle of more than 45 degrees and sometimes recurve toward the stem. The stipules color is between 137A and 138A sometimes lightly suffused especially on the young leaf with between 187D and 183C.

The petiole is average in caliper and usually smooth but sometimes moderately rough. The upper side is deeply grooved with few hairs and stipitate glands on the edges of the grooves. The under side of the petiole is usually smooth but sometimes moderately rough with sometimes very few stipitate glands and very few small prickles. The petiole is about 0.4 to about 1.0 cm in length and about 0.1 to about 0.2 cm in diameter at the widest point. The petiole color is between 145A and 147A usually heavily suffused on the young leaf with between 187B and 183A.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has an upright and rounded moderately spreading medium height growing habit (about 100 to about 130 cm in height and about 60 to about 90 cm spread at the widest point), with full branching. It displays moderately vigorous growth and the canes are of medium caliper for the class.

The color of the major stems is between 146B and 146C. They bear some large prickles that are about 0.9 to about 1.3 cm in length. The large prickles are angled moderately downward with a long narrow oval base; prickle color is between 164A and 166C. The major stem bears few small prickles of similar shape and coloration.

The color of the branches is between 146B and 135A. They bear some large prickles which are of similar size and shape to the large prickles on the major stems; prickle color is between 160A and 153A usually moderately suffused with between 187C and 184B. The branches bear no small prickles.

The color of the new shoots is between 144B and 146A often heavily suffused with between 187B and 183A. The bear some large prickles which are of similar size and shape to the large prickles on the major stems; prickle color is between 160A and 153A usually moderately suffused with between 187C and 184B. The new shoots bear no small prickles.

I claim:

1. A new and distinct Grandiflora rose plant of the variety substantially as described and illustrated herein.

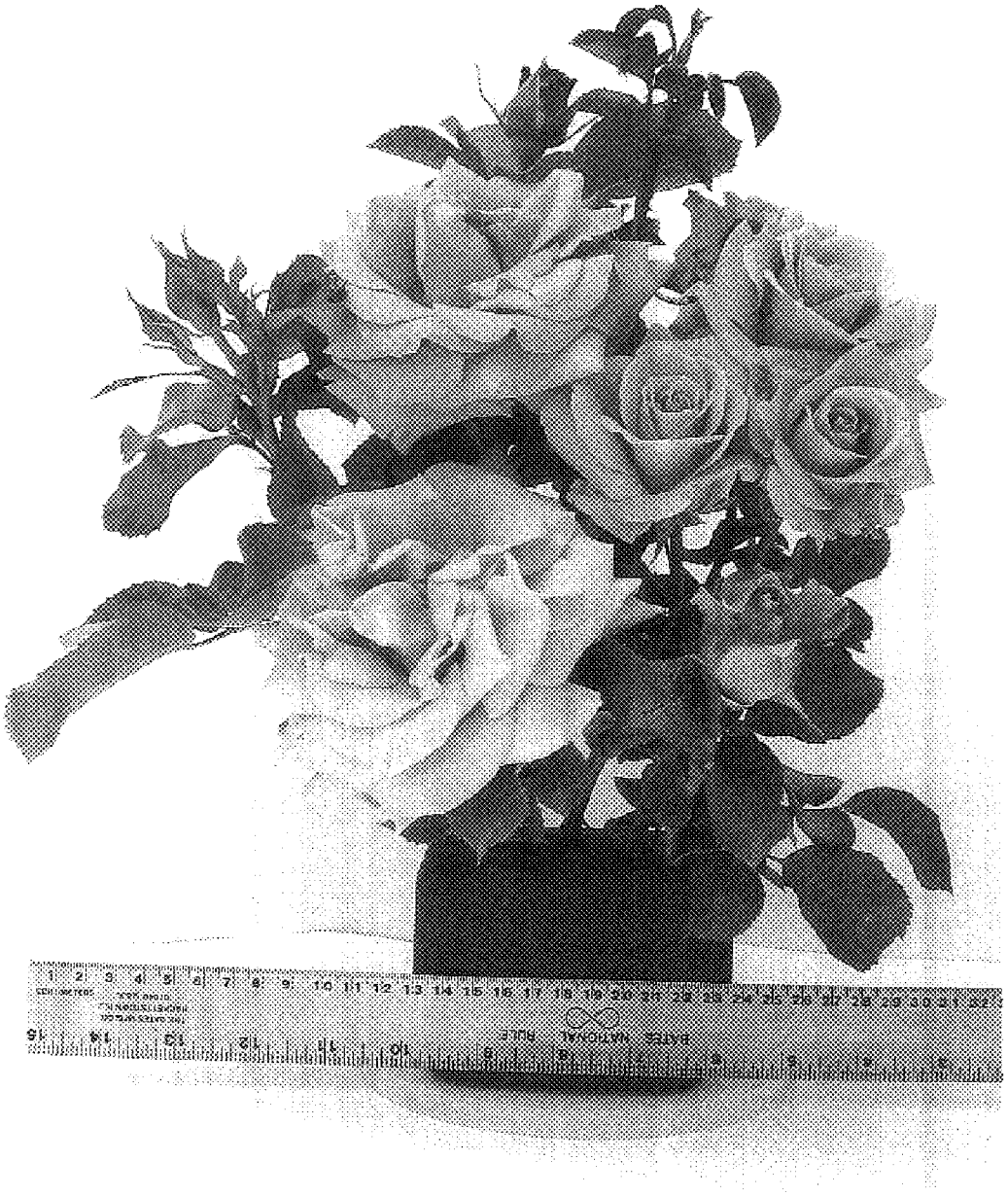

* * * * *